(12) United States Patent
Weston

(10) Patent No.: US 6,681,810 B2
(45) Date of Patent: *Jan. 27, 2004

(54) FILLING DEVICE FOR A NEEDLELESS INJECTOR CARTRIDGE

(75) Inventor: Terence Edward Weston, Suffolk (GB)

(73) Assignee: Aradigm Corporation, Hayward, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/734,549

(22) Filed: Dec. 13, 2000

(65) Prior Publication Data

US 2001/0051793 A1 Dec. 13, 2001

Related U.S. Application Data

(63) Continuation of application No. 08/860,014, filed as application No. PCT/GB95/02913 on Dec. 13, 1995, now Pat. No. 6,174,304.

(30) Foreign Application Priority Data

Dec. 20, 1994 (GB) .............................................. 9425642

(51) Int. Cl.$^7$ ................................................. B65B 1/04
(52) U.S. Cl. ...................... 141/2; 141/311 R; 141/18; 604/500; 604/403; 604/414; 604/82; 604/201; 604/244
(58) Field of Search ............................... 604/500, 131, 604/181–183, 187, 200, 201, 218, 220, 225, 240, 244, 68, 70–72, 82–88, 411, 414, 403, 416, 415; 141/26, 18, 25, 21, 27, 1, 2, 391, 311 R, 392, 387

(56) References Cited

U.S. PATENT DOCUMENTS

| 3,729,031 | A |   | 4/1973  | Baldwin |
| 3,945,383 | A |   | 3/1976  | Bennett et al. |
| 4,010,747 | A |   | 3/1977  | Clark et al. |
| 4,227,528 | A |   | 10/1980 | Wardlaw |
| 4,338,980 | A |   | 7/1982  | Schwebel et al. |
| 4,351,692 | A |   | 9/1982  | Ouellette |
| 4,507,113 | A |   | 3/1985  | Dunlap |
| 4,518,385 | A |   | 5/1985  | Lindmayer et al. |
| 4,568,346 | A |   | 2/1986  | van Dijk |
| 4,662,878 | A |   | 5/1987  | Lindmayer |
| 4,898,209 | A |   | 2/1990  | Zbed |
| 5,062,830 | A |   | 11/1991 | Dunlap |
| 5,171,214 | A | * | 12/1992 | Kolber et al. ................ 206/222 |

(List continued on next page.)

FOREIGN PATENT DOCUMENTS

| EP | 0 201 638 | 11/1986 |
| EP | 0 328 504 | 8/1989 |

(List continued on next page.)

Primary Examiner—Michael J. Hayes
Assistant Examiner—Cris Rodriguez
(74) Attorney, Agent, or Firm—Carol M. LaSalle; Bozicevic, Field & Francis LLP

(57) ABSTRACT

A needleless injector cartridge has an adaptor for introducing fluid from a filling device into an orifice of the cartridge. The adaptor has a frangible connection which is broken to allow removal of the filling device after the cartridge is filled with the fluid.

24 Claims, 5 Drawing Sheets

U.S. PATENT DOCUMENTS

| | | | |
|---|---|---|---|
| 5,188,615 A | 2/1993 | Haber et al. |
| 5,256,142 A | 10/1993 | Colavecchio |
| 5,312,335 A | 5/1994 | McKinnon et al. |
| 5,499,972 A | 3/1996 | Parsons |
| 5,503,627 A | 4/1996 | McKinnon et al. |
| 5,503,628 A | 4/1996 | Fetters et al. |
| 5,779,668 A | 7/1998 | Grabenkort |
| 5,788,670 A | 8/1998 | Reinhard et al. |
| 5,875,976 A | 3/1999 | Nelson et al. |
| 5,938,637 A | 8/1999 | Austin et al. |
| 6,053,890 A | 4/2000 | Moreau Defarges et al. |

FOREIGN PATENT DOCUMENTS

| | | | |
|---|---|---|---|
| EP | 0 412 621 | | 2/1991 |
| EP | 0 526 772 | | 2/1993 |
| EP | 0 737 484 | | 10/1996 |
| FR | 824357 | | 2/1938 |
| HU | 206 016 | | 2/1992 |
| NL | 133435 | * | 9/1971 |
| WO | WO95/03844 | | 2/1995 |
| WO | WO95/24176 | | 9/1995 |
| WO | WO96/15821 | | 5/1996 |
| WO | WO96/28202 | | 9/1996 |
| WO | WO97/13536 | | 4/1997 |
| WO | WO97/22375 | | 6/1997 |
| WO | WO97/36785 | | 10/1997 |
| WO | WO98/12121 | | 3/1998 |
| WO | WO00/15281 | | 3/2000 |
| WO | WO00/35520 | | 6/2000 |

* cited by examiner

FILLING DEVICE FOR A NEEDLELESS INJECTOR CARTRIDGE

This application is a Continuation of Application Ser. No. 08/860,014 filed Jul. 30 1997, which is now U.S. Pat. No. 6,174,304, a 371 of International Application Serial No. PCT/GB95/02913 filed Dec. 13, 1995.

The present invention relates generally to hypodermic injection devices, and is for use with needleless injectors in particular.

Needleless injectors are used as an alternative to hypodermic syringes for delivering liquid drugs and medicaments directly through the patient's skin and into the tissues without using a needle. Such injectors consist of a piston pump, drive by a spring or gas, which ejects the drug through a small discharge orifice at sufficient rate and pressure to pierce the skin and enter the tissue through the hole thus formed.

In WO 95/03844, a needleless injector is disclosed which uses efficient energy storage and release means to provide a very compact and easy-to-use device, and the present invention is intended primarily for use with that device, although of course it could be adapted for use with alternative injectors. Ideally, a needleless injector would be provided to the end user pre-filled with the drug, self-powered, and ready for immediate use. The pre-filling of the injector would preferably be done by the drug manufacturer, thereby ensuring sterility, correct dose, and conformity to the approved specification.

However, whilst this is perfectly feasible for liquid-stable drugs such as heparin and some vaccines, for example, many drugs consist of two components, e.g. a lyophilised drug and its solvent. These drugs have a short shelf-life in liquid forms, and must be re-constituted and used immediately. Other drugs, which may be already in liquid form, are supplied in bulk to a pharmacy for example, and the pharmacist may be required to load the drug into the injector.

There is a long-standing requirement for a single dose disposable needleless injector which may be externally filled, and many inventions aim to provide external loading methods—e.g. WO89/08469 (Parsons). Most such devices are complicated and costly, and are inconvenient to use. With the present trend towards single use disposable needleless injectors, the filling device ought to be very simple to use, and sufficiently inexpensive so that it may be disposed of with the injector.

Another invention, by Lindmayer, U.S. Pat. No. 4,518,385, is for a disposable syringe which is filled by the user in a conventional manner. After filling, the hollow filling needle is removed or broken off, and the syringe body is inserted into the power unit. The syringe body becomes the needleless dispensing member, and thus the syringe has a dual function. Although U.S. Pat. No. 4,518,385 does go some way in simplifying the loading process, there is still a substantial requirement for the user to exercise skill and judgement in using the device. Moreover, the syringe is intended for use with a multiple use power unit or actuator, which is complex and expensive.

The present invention seeks to overcome the limitations of prior art injectors, and provides a simple adaptor for use with a standard hypodermic syringe, which adaptor may be removed after filling the injector together with the syringe. After use, the adaptor covers the end of the needle to prevent or reduce likelihood of pricking the user.

Thus, according to a first aspect of the invention there is provided an adaptor for enabling a fluid to be introduced from an outlet of a filling device into an orifice of a needleless injector cartridge, comprising a first portion for engagement with the cartridge, and a device-engaging second portion for engagement with the filling device, whereby to maintain the outlet of the filling device in fluid communication with the orifice of the cartridge, the said first and second portions being connected to one another by a detachable connection.

According to a second aspect of the invention there is provided a needleless injector cartridge in combination with an adaptor for enabling a fluid to be introduced from an outlet of a filling device into an orifice of the cartridge, wherein the adaptor comprises a device-engaging portion whereby to maintain the outlet of the filling device in fluid communication with the orifice of the cartridge, the said first and second portions being connected to one another by a detachable connection.

With the syringe assembled to the needleless injector, the injectate may be transferred into the cartridge from the syringe, through the discharge orifice in the cartridge, thus to displace the cartridge piston by hydraulic pressure. Stop means is preferably provided to limit the displacement of the piston, so that the amount of injectate transferred into the injector cartridge is predetermined.

Another aspect of the invention is to provide for the reconstitution of a lyophilised drug. In a preferred embodiment, the lyophilised drug is stored in the drug cartridge between the discharge orifice and piston, so that the introduction of a liquid solvent through the orifice will dissolve the lyophilised drug and displace the piston by hydraulic pressure to a pre-determined stop.

The connection between the syringe guide and drug cartridge or cartridge retainer is preferably provided by a frangible joint or other detachable connection. After transferring the injectate, the syringe is given a sharp sideways pull which causes the guide to break away from the cartridge or its retainer at the frangible joint. Preferably the needle is protected by remaining inside the resilient seal, which itself remains attached to the syringe guide.

The invention in its various aspects is capable of providing a very safe, simple and convenient means of filling a pre-assembled, self-powered needleless injector to a pre-determined volume, with safe disposal of the filling syringe thereafter. The safety aspect is enhanced if the hypodermic syringe needle is blunt.

A preferred embodiment will be described with reference to the accompanying drawings, in which.

For the sake of simplicity, like parts are given the same numbers.

Figure 1:
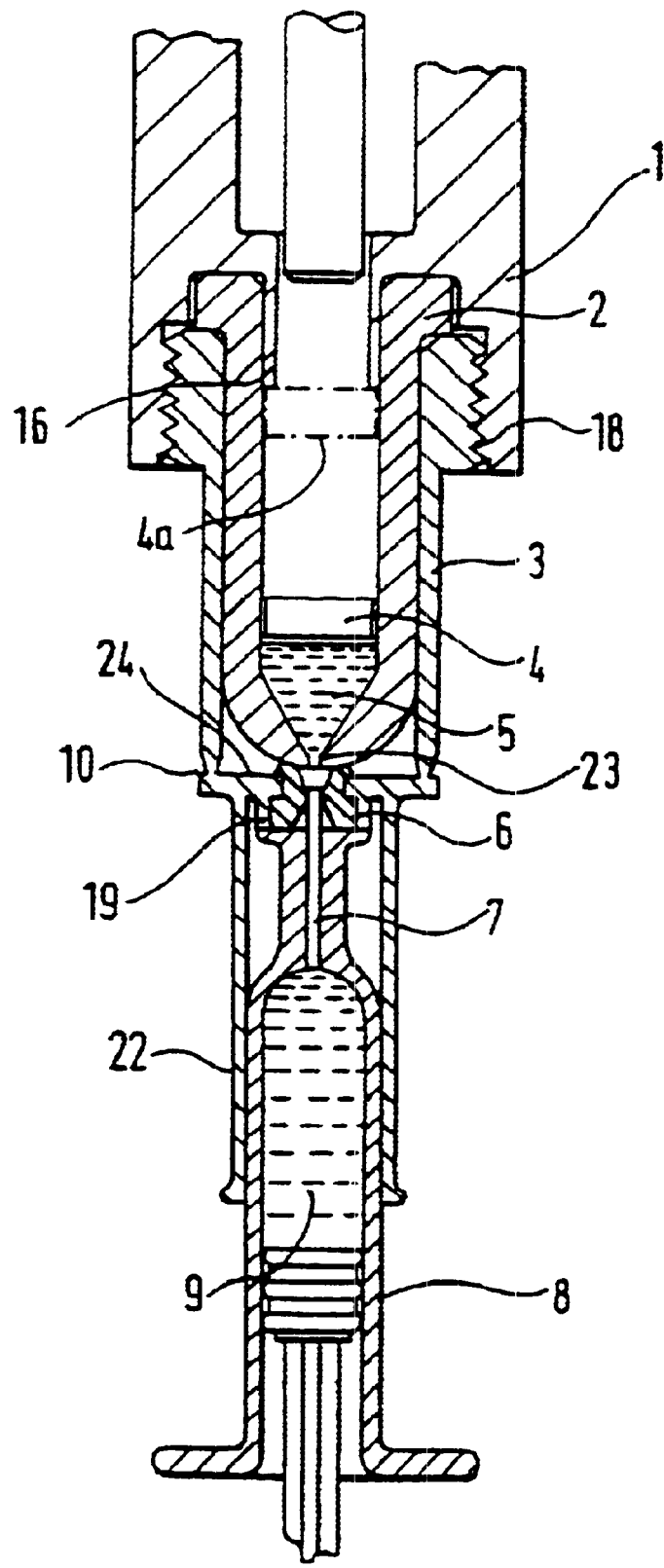
FIG. 1 shows a cross-section through a needleless injector containing a lyophilised drug and hypodermic syringe assembled to the injector.
Figure 2A:
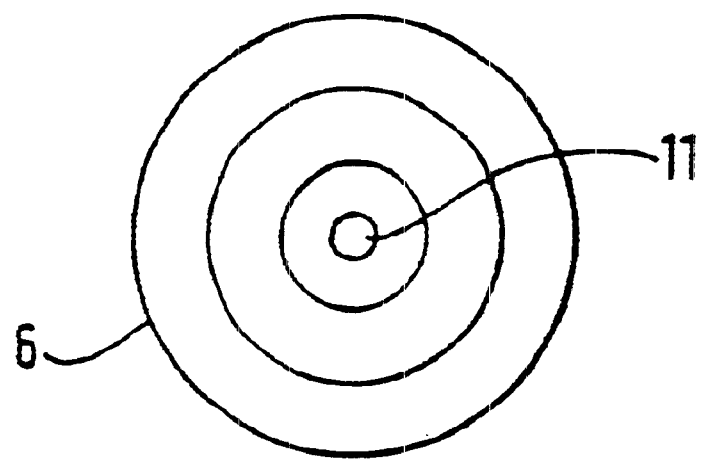
FIGS. 2a and 2b show a resilient seal, in plan view and longitudinal section, respectively.
Figure 2B:
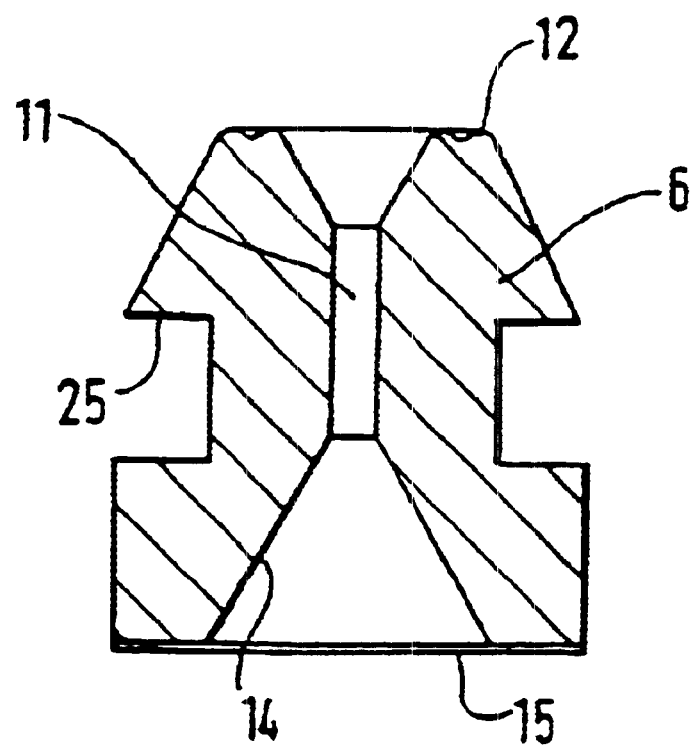

Referring to FIG. 1, a needleless injector body 1 contains a drug cartridge 2 retained by a sleeve 3 having a threaded flange 18. The cartridge 2 contains a lyophilised drug 5, preferably preformed to fit closely to the internal container of the drug cartridge, and held firmly in place by a piston 4, adjacent to a discharge orifice 23. A syringe guide 22 is frangibly attached by a frangible connection 10 to the retaining sleeve 3. The syringe guide 22 is preferably tubular, open at one end to receive a syringe 8, and having a partial end wall 24. Inserted in a concentric hole in the end wall 24 is a resilient seal 6 (see also FIGS. 2a and 2b) which is biased to form an hydraulic seal around the discharge orifice 23 of the cartridge 2. Referring to FIG. 2, the resilient seal 6 has a hole 11 to sealingly receive the hypodermic needle 7 (FIG. 1) of the syringe 8, and may have circumferential ribs 12 to improve the sealing efficiency on the cartridge 2. A conical entry hole 14 helps to guide the needle into the hole 11. Preferably, the conical hole 14 is sealed with a frangible diaphragm 15, which may be made from a laminate of aluminium foil and plastics, or other material which is impervious to water vapour and capable of withstanding a pressure differential of up to 900 mbar. Retaining lip 25 serves to hold the seal 6 in the end wall 24 of the syringe guide 22 (FIG. 1).

Referring to FIGS. 1 and 2, the filled syringe 8 is loaded into the open end of the syringe guide 22; the guide is long enough to align the syringe body so that the needle 7 is approximately concentric with the conical hole 14 in the seal 6. By pushing on the syringe body, the needle 7 ruptures the frangible diaphragm 15, and is guided by the conical hole 14 to enter the hole 11. The syringe body comes to rest on a rim 19, which extends axially from the end wall 24 of the syringe guide 22. The rim 19 may also locate the seal 6, so that the end of the needle 7 just touches the orifice 23 in cartridge 2. The bore of the needle 7 is now in hydraulic contact with the inside of the drug cartridge 2 via the orifice 23, and by acting on the plunger of the syringe 8, solvent 9 will be transferred into the drug cartridge 2. The hydraulic pressure created within the syringe 8 causes the piston 4 to move in the cartridge 2 until it stops at position 4a against an abutment 16 formed on the injector body. During this time, the turbulence of the inflowing solvent 9 will agitate the lyophilised drug 5, helping it to dissolve. An agitator (not shown) may be previously loaded together with the drug 5, so that by shaking the needleless injector after filling, rapid dissolution of the drug 5 will result.

Figures 5A, 5B:
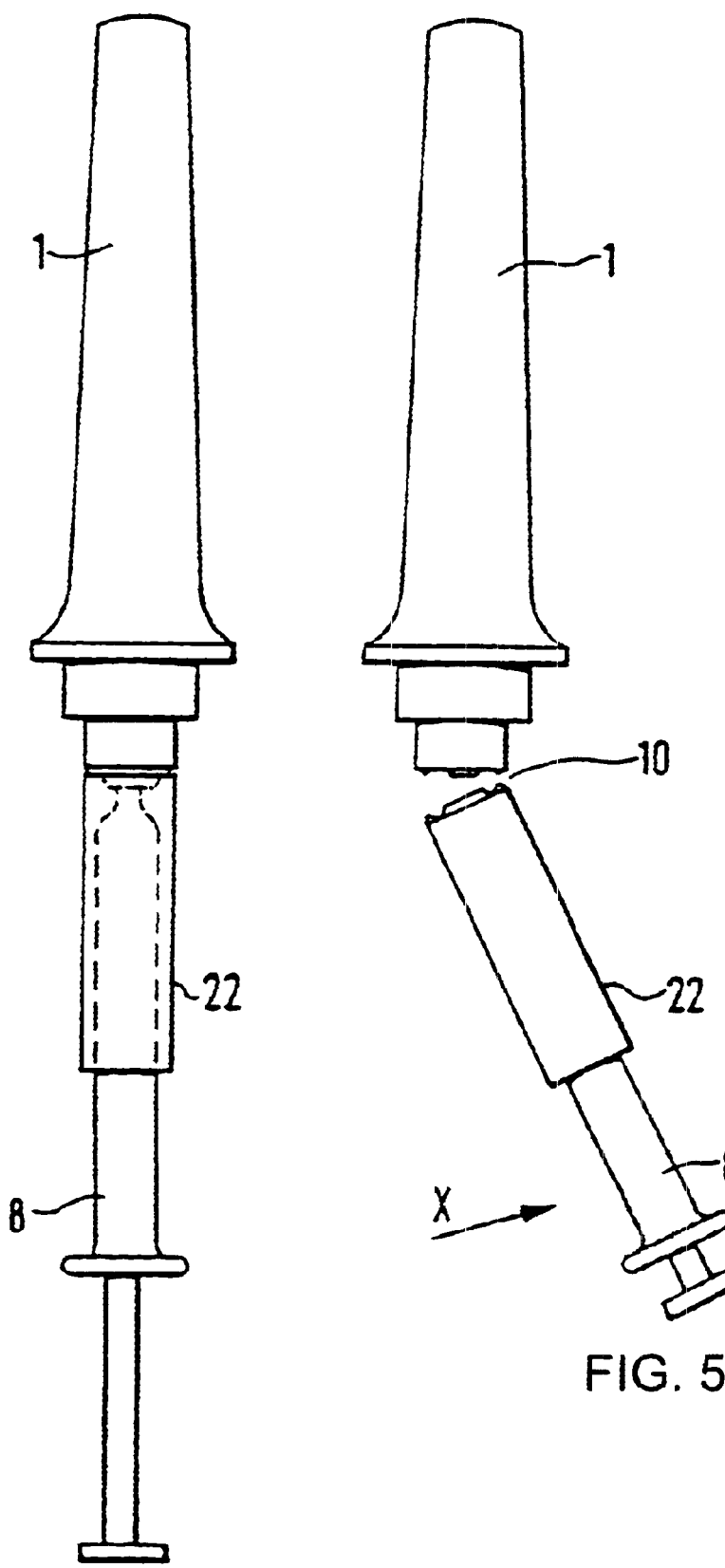
FIGS. 5a and 5b are general views of an injector before and after filling.

After filling the injector, the syringe 8 and guide 22, whilst still assembled together, may be snapped off of retaining sleeve 3 at the frangible connection 10, by pulling it sharply sideways in direction X relative to the injector, as shown in FIG. 5b.

Figure 3:
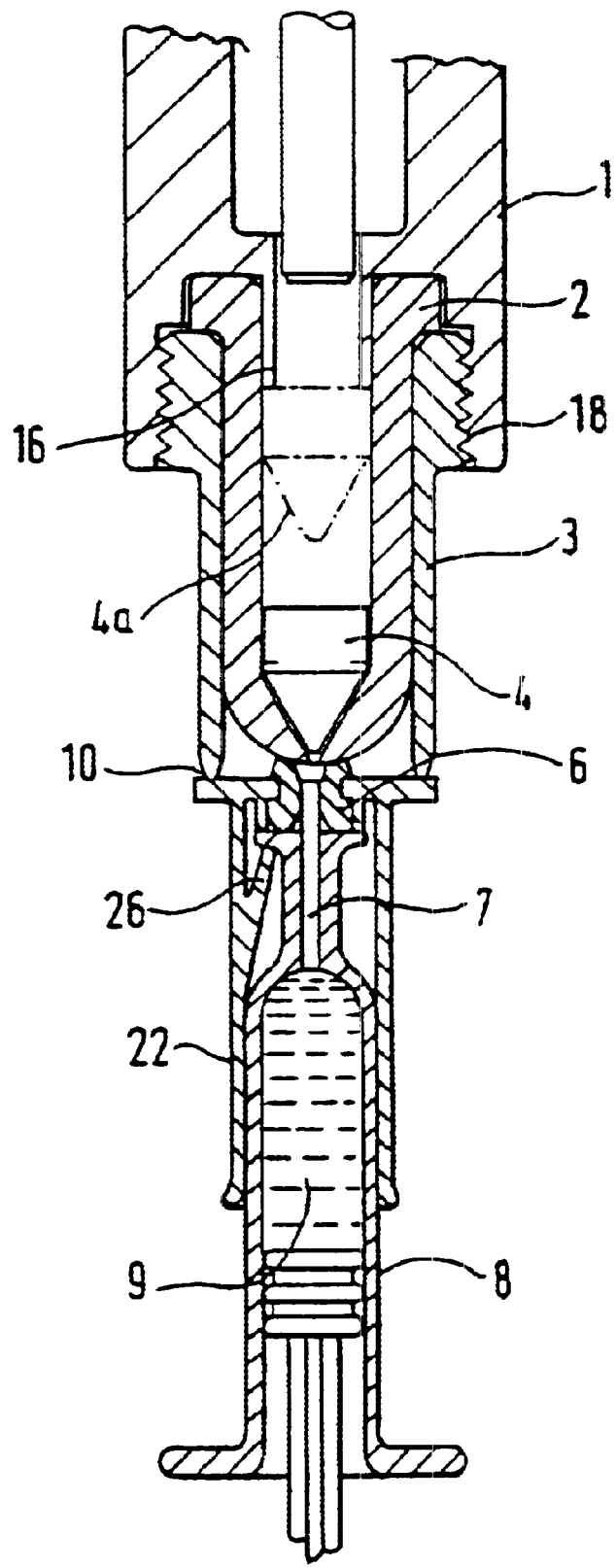
FIG. 3 shows a cross-section through a needleless injector with a hypodermic syringe attached, for filling the injector with a liquid drug, which may be reconstituted.

Referring to FIG. 3, a similar construction to that already described is shown, except that the drug container 2 does not at this stage contain any drug (e.g. lyophilised drug) and the piston 4 is shaped to conform closely to the internal profile of the discharge end of container 2. This embodiment is for use with a hypodermic syringe, as before, but the drug to be transferred is pre-mixed. A further enhancement shown in FIG. 3, and applicable to all embodiments, is a resilient projection 26, extending from the inside wall of the guide 22, which serves to prevent removal of the syringe 8 from the guide 22 after insertion.

In the embodiments described, the drug cartridge is a separate component, and may be made from glass, metal, or plastic. In order to withstand the high pressure produced during injection, the retaining sleeve 3 may act as a reinforcing member to the drug cartridge 2, which then may be of a more lightweight construction than otherwise possible.

Figure 4:
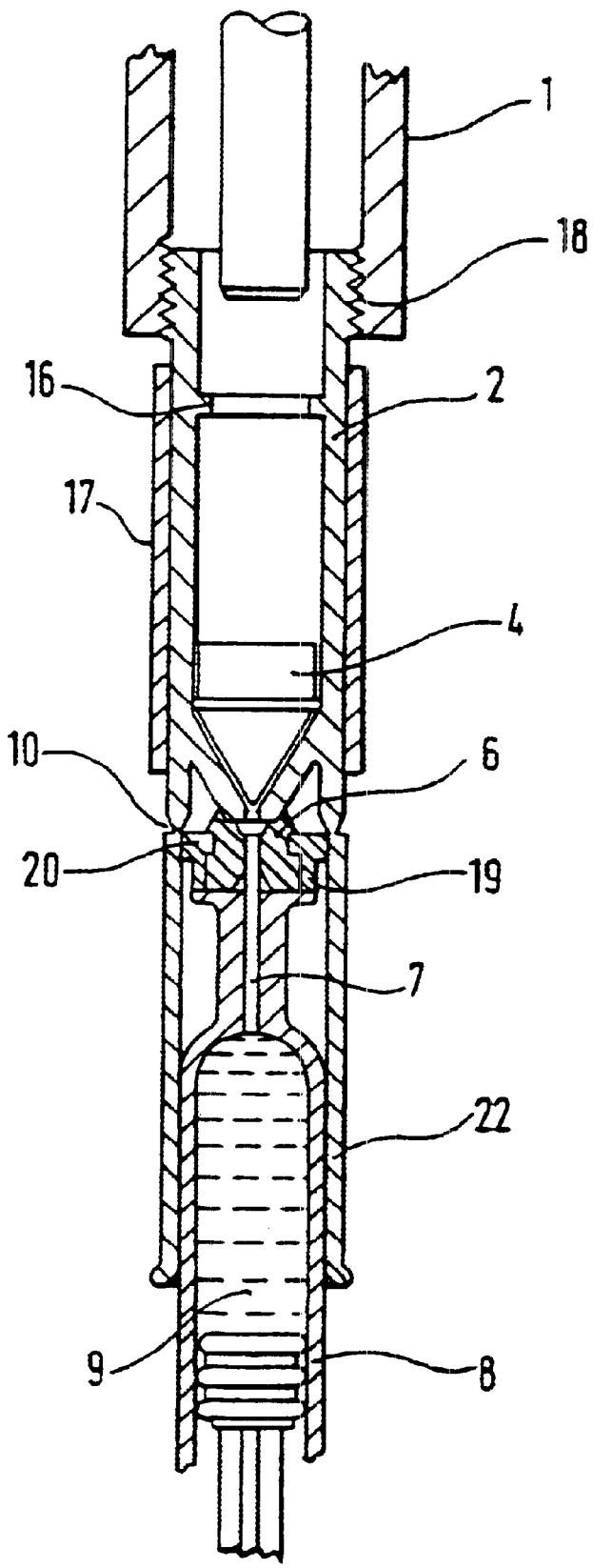
FIG. 4 shows a needleless injector drug cartridge with integral syringe guide.

A further embodiment is shown in FIG. 4, in which the drug cartridge 2 is made with thread 18 for screwing directly on injector body 1. This embodiment is preferably manufactured in a plastics material, and the syringe guide 22 may be conveniently moulded integrally with the cartridge 2, with the frangible connection 10 between the two elements. If the material strength is too low for a reasonable wall thickness to the cartridge, the cartridge may be fitted with a reinforcing sleeve 17 either after moulding, or as an-insert during moulding. The abutment 16 may be conveniently moulded on the cartridge 2, either as a continuous ring or as small projections. Alternatively, the abutment may be an interference-fit ring in the cartridge 2 to achieve the same objective of limiting the stroke of the piston 4. Piston 4 is configured to fit closely to the internal profile of the discharge end of the cartridge 2. To avoid undue difficulties in moulding, the resilient seal 6 may be retained in a separate holder 20, which may be an interference fit or retained by cooperating lugs in the guide 22, so as to bias seal 6 to form an hydraulic seal on the discharge end of the cartridge 2. This embodiment may be adapted to contain an lyophilised drug, similarly to the embodiment shown in FIG. 1, and the piston 4 may be shaped with a flat end face.

A feature of all the embodiments described above is that the hypodermic syringe 8 and its guide 22 are snapped off together after filling the injector, and the seal 6 remains in situ in the guide 22 to reduce the risk of injury from the end of needle 7. This risk may be further reduced by having a blunt or rounded end to the needle instead of the usual sharp point. Of course, it may be that a commercial hypodermic syringe is inconvenient, if, for example, more than one needleless injector is to be filled from a large filled syringe. Such procedures may be necessary in hospitals and pharmacies, where the injector is to be used within a short time of filling. In these cases, the guide 22 is left in place and the hole 11 in the seal 6 may be self closing after removal of the filling needle 7, in order to maintain at least short term sterility of the drug contained in the injector. When the injector is required for use, the guide 22 is snapped off as previously described, taking the seal 6 with it.

For all embodiments, the preferred material for piston 4 is PTFE or similar fluoropolymer having a compressive strength that is highly dependent on the rate of application of force at room temperature. Thus the piston 4 may easily deform when pushed past the abutment 16 (FIG. 4) and spring back to seal on the walls of the cartridge 2, but when the injection force is applied at a high rate to the piston 4, it has insufficient time to deform and will maintain its sealing properties throughout the injection.

Whilst the embodiments described specify screw thread means of retaining the drug cartridge onto the injector body, it would be equally feasible to use snap-fit retaining means. Furthermore, the retaining means may use cut-outs or other mechanical keying means to ensure the correct matching of drug cartridge to injector body. It is preferred that the drug cartridge is not easily removed from the injector power unit after performing an injection, except by means of a tool.

Many variations of the basic invention are possible. For example, the injector and syringe may be supplied as part of a kit with which the user must reconstitute a lyophilised drug for self administration. The syringe containing the solvent may be pre-inserted in the syringe guide, so that the user merely has to push the syringe slightly further into the guide to break the seal, and operate the syringe plunger until the solvent ceases to be transferred, that is, when the injector piston reaches the abutment in the cartridge.

It may be seen therefore that the present invention enables a needleless injector to be filled with the absolute minimum of skill, using a very inexpensive and familiar hypodermic syringe or similar device.

What is claimed is:

1. A needleless injector cartridge in combination with an adaptor for to be introduced from an outlet at the distal end of a filling device into the cartridge, the cartridge comprising a cartridge body having first and second ends, with a piston longitudinally slidable within the body, the cartridge body and piston being adapted to define together a fluid chamber, the cartridge body defining at its first end an orifice sized to permit fluid to be expelled therethrough, during use, at a velocity sufficient to effect needleless injection, wherein the adaptor comprises a first device-engaging portion whereby to maintain the outlet at the distal end of the filling device in fluid communication with said orifice, to permit fluid to be introduced by the filling device, through said orifice, into said fluid chamber, and a second portion in engagement with the cartridge, the first and second portions being connected to one another by a frangible connection, whereby the first portion can be snapped off the second portion prior to use.

2. The cartridge/adaptor combination according to claim 1, further including a sealing means for effecting a seal between the filling device outlet and the cartridge orifice.

3. The cartridge/adaptor combination according to claim 2, wherein the sealing means comprises a sealing member having respective conically tapering passages at opposite ends thereof and means communicating the passages with one another.

4. The cartridge/adaptor combination according to claim 2, wherein the sealing means is carried by support means connected to the said device-engaging portion, so as to remain connected thereto when the said frangible connection is broken.

5. The cartridge/adaptor combination according to claim 4, wherein said support means includes a means for engagement with the distal end of the filling device to align the filling device outlet with the cartridge orifice.

6. An adaptor or cartridge/adaptor combination according to claim 1, wherein the device-engaging portion comprises means for preventing removal of the filling device from the device-engaging portion.

7. An adaptor or cartridge/adaptor combination according to claim 6, wherein said preventing means comprises a resilient projection adapted to engage behind the distal end of the filling device.

8. The cartridge/adaptor combination according to claim 1, wherein the filling device is a syringe.

9. The cartridge/adaptor combination according to claim 1, wherein the device-engaging portion comprises a sleeve in which the filling device is received.

10. A needleless injector cartridge in combination with an adaptor for enabling a fluid to be introduced from an outlet of a filling device into the cartridge, the cartridge comprising a cartridge body having first and second ends, with a piston longitudinally slidable within the body, the cartridge body and piston being adapted to define together a fluid chamber, the cartridge body defining at its first end an orifice sized to permit fluid to be expelled therethrough, during use, at a velocity sufficient to effect needleless injection, wherein the adaptor comprises a device-engaging member for maintaining the outlet of the filling device in fluid communication with said orifice, to permit fluid to be introduced by the filling device, through said orifice, into said fluid chamber, the device-engaging member being connected to the cartridge by a frangible connection, whereby the device-engaging member can be snapped off the cartridge prior to use.

11. The cartridge/adaptor combination according to claim 10, further including a reinforcing sleeve which surrounds at least part of the cartridge.

12. The cartridge/adaptor combination according to claim 10, wherein the cartridge comprises a cartridge body with a longitudinally slidable piston therein and wherein an abutment is provided within the cartridge body for limiting movement of the piston away from the cartridge orifice.

13. The cartridge/adaptor combination according to claim 10, wherein the cartridge carries a screw thread for engagement with a mating thread on an injector.

14. The cartridge/adaptor combination according to claim 10, wherein the cartridge is sealed with an imperforate, frangible seal.

15. The cartridge/adaptor combination according to claim 14, wherein the said frangible seal is capable of withstanding a pressure differential of up to 900 mbar.

16. The cartridge/adaptor combination according to claim 10, further including a sealing means for effecting a seal between the filling device outlet and the cartridge orifice.

17. A method of introducing fluid from an outlet of a filling device into a needleless injector cartridge, comprising the steps of:

(a) providing, in combination, a cartridge comprising a cartridge body having first and second ends, with a piston longitudinally slidable within the body, the cartridge body and piston being adapted to define together a fluid chamber, the cartridge body defining at its first end an orifice sized to permit fluid to be expelled therethrough, during use, at a velocity sufficient to effect needleless injection, and an adaptor which comprises a first device-engaging portion and a second portion in engagement with the cartridge, the first and second portions being connected to one another by a frangible connection, whereby the first portion can be snapped off the second portion prior to effecting a needleless injection;

(b) engaging the said first device-engaging portion of the adaptor with the outlet of the filling device, so as to maintain said outlet in fluid communication with said orifice; and (c) introducing fluid from the outlet of the filling device, through said orifice, into said fluid chamber.

18. A method according to claim 17, wherein the outlet orifice of the cartridge body is sealed with an imperforate frangible seal.

19. A method according to claim 1, wherein the said frangible seal is capable of withstanding a pressure differential of up to 900 mbar.

20. A method according to claim 17, wherein introduction of the fluid causes the piston to move longitudinally.

21. A method of introducing fluid from an outlet of a filling device into a needleless injector cartridge, comprising the steps of (a) providing, in combination, a cartridge comprising a cartridge body having first and second ends, with a piston longitudinally slidable within the body, the cartridge body and piston being adapted to define together a fluid chamber, the cartridge body defining at its first end an orifice sized to permit fluid to be expelled therethrough, during use, at a velocity sufficient to effect needleless injection, and an adaptor which comprises a device-engaging member, the device-engaging member being connected to the cartridge by a frangible connection, whereby the device-engaging member can be snapped off the cartridge prior to effecting a needleless injection;

(b) engaging the said device-engaging member with the outlet of the filling device, so as to maintain said outlet in fluid communication with said orifice; and (c) introducing fluid from the outlet of the filling device, through said orifice into aid fluid chamber.

22. A method according to claim 21, wherein the outlet orifice of the cartridge body is sealed with an imperforate frangible seal.

23. A method according to claim 22, wherein the said frangible seal is capable of withstanding a pressure differential of up to 900 mbar.

24. A method according to claim 21, wherein introduction of the fluid causes the piston to move longitudinally.

* * * * *

UNITED STATES PATENT AND TRADEMARK OFFICE
CERTIFICATE OF CORRECTION

PATENT NO.     : 6,681,810 B2
DATED          : January 27, 2004
INVENTOR(S)    : Weston Terence Edward et al.

It is certified that error appears in the above-identified patent and that said Letters Patent is hereby corrected as shown below:

Column 4,
Line 67, insert -- enabling a fluid -- between "for" and "to".

Signed and Sealed this

Twenty-second Day of June, 2004

JON W. DUDAS
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 6,681,810 B2 | Page 1 of 1 |
| APPLICATION NO. | : 09/734549 | |
| DATED | : January 27, 2004 | |
| INVENTOR(S) | : Terence Edward Weston | |

It is certified that error appears in the above-identified patent and that said Letters Patent is hereby corrected as shown below:

Col. 6, at line 20, please correct the word "needless" to read --needleless--

Signed and Sealed this

Fifteenth Day of September, 2009

David J. Kappos
*Director of the United States Patent and Trademark Office*